United States Patent

Cipriani et al.

Patent Number: 4,812,502
Date of Patent: Mar. 14, 1989

[54] OLIGOMER FLAME-RETARDING ADDITIVE, PROCESS FOR ITS PREPARATION AND ITS USE FOR ENDOWING A LINEAR POLYESTER WITH SELF-EXTINGUISHING CHARACTERISTICS

[75] Inventors: Gioacchino Cipriani, Milan; Armando Mariano, Matera, both of Italy

[73] Assignee: Enichem Sintesi, S.p.A., Palermo, Italy

[21] Appl. No.: 70,355

[22] Filed: Jul. 7, 1987

[30] Foreign Application Priority Data

Jul. 23, 1986 [IT] Italy ................. 21228 A/86

[51] Int. Cl.[4] ............... C07F 9/38; C07F 9/40; C08K 5/53; C08G 79/04
[52] U.S. Cl. ................. 524/125; 524/126; 528/287; 558/131; 558/155; 558/88
[58] Field of Search .......... 524/125, 126; 528/287; 558/207, 216, 88, 119, 133, 155

[56] References Cited

U.S. PATENT DOCUMENTS

| | | | |
|---|---|---|---|
| 3,020,306 | 2/1962 | Birum | 524/125 |
| 3,058,941 | 10/1962 | Birum | 524/125 |
| 3,065,183 | 11/1962 | Temin | 524/125 |
| 3,853,819 | 12/1974 | Herwig et al. | 528/287 |
| 4,517,355 | 5/1985 | Mercati et al. | 528/287 |

FOREIGN PATENT DOCUMENTS 59-91122  5/1984  Japan.
59-91716 10/1984  Japan.

*Primary Examiner*—Veronica P. Hoke
*Attorney, Agent, or Firm*—Hedman, Gibson, Costigan & Hoare

[57] ABSTRACT

An oligomer flame-retarding additive can be defined by the general formula

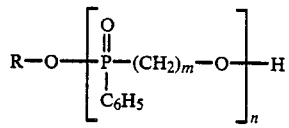

wherein:
R is the hydrogen atom, or a linear or branched alkyl radical, containing from 1 to 6 carbon atoms;
m takes the value 1, 2 or 3;
n takes a value, or an average value, comprised within the range of from 2 to 50.

Such an additive is obtained by means of the oligomerization of a hydroxyalkylenephenylphosphinic acid or of a related alkyl ester thereof.

According to another form of practical embodiment, the flame-retarding additive is the product of co-oligomerization of a hydroxyalkylenephenylphosphinic acid, or of a related alkyl ester thereof, with a phenylphosphonic acid or a related alkyl ester thereof.

Such oligomer additives are used for endowing a linear polyester with self-extinguishing characteristics.

28 Claims, No Drawings

OLIGOMER FLAME-RETARDING ADDITIVE, PROCESS FOR ITS PREPARATION AND ITS USE FOR ENDOWING A LINEAR POLYESTER WITH SELF-EXTINGUISHING CHARACTERISTICS

The present invention relates to an oligomer flame-retarding additive, to the process for its preparation and to its use for endowing a linear polyester with self-extinguishing characteristics.

It is known that the linear polyesters are obtained in the art by polycondensing, in the presence of suitable catalysts, bicarboxy aromatic acids with alkylene glycols, and, in particular, terephthalic acid, or a dimethyl ester thereof, with ethylene glycol. The so obtained linear polyesters are valuable products, in that they constitute starting materials for such interesting manufactured articles are fibres, films, sheets and other articles.

A drawback of these articles is their flammability, with all of the consequent risks, in particular in the textile sector and in the electrotechnical sector.

Hence, various flame-retarding agents have been proposed for application to the linear polyester by a surface treatment, or by the addition during the processing step, e.g., during the spinning step.

Thus, for example, tris-dibromopropyl phosphate has been used in the textile sector as a finishing agent. But its resistance to washings is not completely satisfactory, and it shows, furthermore, a certain toxicity. The addition of brominated flame-retarding agents during the spinning step is furthermore known. However, difficulties exist in finding brominated compounds which are stable and free from phenomena of decomposition under the temperature conditions typical of the spinning process, and of the other fibre processing steps.

In the art, the addition has also been proposed of particular reactive monomers containing phosphorus during the step of polycondensation of the aromatic bicarboxy acid with the alkylene glycol. With such monomers, linear polyesters are obtained, which show acceptable values of flame resistance, with amounts of phosphorus (expressed as the element) which can be, in some cases, as low as 0.5–0.8% by weight, as it is disclosed, e.g., in U.S. Pat. No. 4,517,355 issued on May 14, 1985.

These reactive monomers containing phosphorus are however compounds having a low, or relatively low, molecular weight, which can hence involve problems of volatility when they are used during the step of polycondensation of the linear polyester, which takes place at a high temperature, and under a high vacuum.

Furthermore, the useof these phosphorus containing monomers is limited to their addition during the step of polycondensation of the linear polyester, in that their blending with the already formed polyester causes a significant lowering in the viscosity of this latter, with a consequent worsening of the quality of the manufactured items obtained from such polymers, or with the impossibility of submitting the same polymers to such processes as the spinning process.

Therefore the need is strongly felt in the art, of having available a flame-retarding additive, containing phosphorus, free from the characteristics of volatility, and capable of endowing the linear polyester with self-extinguishing characteristics, both when it is added during the polycondensation step, and when it is added to the already formed linear polyester, and of stably remaining in the same polyester, without impairing the characteristics thereof.

The present Applicant has found now that said needs of the art can be fulfilled by adopting a flame-retarding agent containing phosphorus, and having an oligomer nature.

Accordingly, the present invention relates to an oligomer flame-retarding additive to be defined by the general formula:

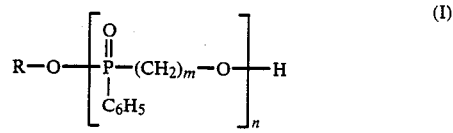

wherein:

R is a hydrogen atom, or a linear or branched alkyl radical, containing from 1 to 6 carbon atoms;

m takes the value 1, 2 or 3;

n takes a value, or an average value, comprised within the range of from 2 to 50.

In the preferred form of practical embodiment, in the above formula (I) R represents the hydrogen atom, m is 1 and n varies within the range of from 20 to 50.

Such a flame-retarding additive is obtained, according to the present invention, by heating a hydroxyalkylenephenylphosphinic acid, or an alkyl ester thereof:

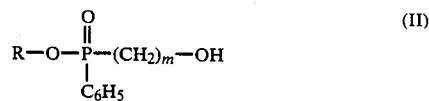

wherein R and m have the above indicated meaning; at a temperature comprised within the range of from 140° to 180° C., under a pressure of from 0.1 to 200 mm$_{Hg}$, with the reaction water or the aliphatic alcohols which is formed as a reaction byproduct during the polycondensation being removed, until the desired value for n in the above formula (I) is obtained.

In case R in the above formula (II) is the hydrogen atom, the reaction can be carried out in the presence of such a solvent as xylene, for the purpose of removing water as an azeotropic mixture during the course of the condensation.

Also small amounts of catalysts can be used, which favour the oligomerization of the hydroxyalkylenephenylphosphinic acid or ester, such as, e.g., tin, germanium, titanium, manganese, magnesium and zinc compounds. The alkali metal alkoxides, e.g., sodium alkoxide, are efficacious in the oligomerization of hydroxyalkylenephenylphosphinic acid.

The oligomerization time is the time required for obtaining the desired value for n in above formula (I).

Under the above indicated conditions, the reaction time can generally vary within the range of from 1 to 5 hours.

According to another form of practical embodiment of the present invention, the flame-retarding additive is the product of co-oligomerization of a hydroxyalkylenephenylphosphinic acid, or of a related alkyl ester thereof, having the above formula (II), with a phenylphosphonic acid or a related alkyl ester thereof, which can be defined by the general formula:

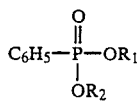

(III)

wherein: $R_1$ and $R_2$ are equal to, or different from, each other, and each of them represents a hydrogen atom, or a linear or branched alkyl radical, containing from 1 to 6 carbon atoms.

In the preferred form of practical embodiment, the hydroxyalkylenephenylphosphinic acid (II), in which R represents the hydrogen atom, and m is 1, is co-oligomerized with the phenylphosphonic acid (III) wherein both $R_1$ and $R_2$ represent the hydrogen atom.

Said co-oligomerization is carried out within the general range of oligomerization conditions as reported above, and yields similar products.

The oligomer flame-retarding agent so obtained can be added to the prepolymer of the linear polyester, during the polycondensation step.

More particularly, in the preparation of the self-extinguishing linear polyester of the present invention, a low molecular weight pre-condensate is first formed, by starting from the aromatic bicarboxy acid, or from a related di-lower-alkyl ester thereof (generally, terephthalic acid, or dimethyl terephthalate) and from the alkylene glycol (generally, ethylene glycol).

To the precondensate, the suitable amount is then added of the oligomer flame-retarding additive, and finally the polycondensation is carried out until the values of molecular weight typical for linear polyesters are reached.

Typically, said polycondensation is carried out at 270°–280° C., with pressure being reduced down to values of the order of 0.1 torr, or less.

According to another form of practical embodiment of the present invention, the oligomer flame-retarding additive is added to the linear polyester in the molten state (270°–290° C.), and is homogenized with it.

In particular, the addition can be carried out at the end of the polycondensation step, before the linear polyester is transformed into granules, or it can take place immediately before the spinning step.

According to a further form of practical embodiment of the present invention, a composition (master) is prepared of the linear polyester, which contains a high amount of oligomer flame-retarding additive, e.g., up to about 20–30% by weight. This composition, which can be obtained both by means of the procedure of copolymerization of the oligomer additive with the prepolymer of the linear polyester, and by means of the blending and homogenization of the additive with the molten linear polyester, is added in its turn to the linear polyester for supplying the desired self-extinguishing characteristics. It should be observed that in any case self-extinguishing linear polyesters are obtained, wherein the phosphorus compound is chemically bonded and evenly distributed throughout the macromolecular chain.

The oligomer flame-retarding additives of the present invention are products which show a softening temperature which is a function of their molecular weight, and are storage-stable and easily-handled products.

The self-extinguishing linear polyesters of the present invention contain an amount of phosphors (as expressed as the element) which can vary within the range of from 0.5 to 0.8% by weight, and is preferably of the order of from 0.5 to 0.65% by weight.

In the above disclosure, oligomer compounds and co-oligomer compounds of hydroxylkylenephenylphosphinic acid, or of a related alkyl ester thereof, have been disclosed.

However, the fact should be appreciated that similar oligomer or co-oligomer compounds can be obtained from such an acid, or related ester, in which the phenyl group is substituted by a group selected from:

phenyl substituted with one or more substituents from the group of $(C_1-C_4)$-alkyl, $(C_1-C_4)$-alkoxy, or halogen, in particular chlorine and bromine, substituents;

naphthyl;

naphthyl substituted with one or more substituents from the group of $(C_1-C_4)$-alkyl, $(C_1-C_4)$-alkoxy, or halogen, in particular chlorine and bromine, substituents;

$(C_1-C_4)$-alkyl.

Furthermore, the flame-retardant agents of the present invention can be used in polyesters different from polyethyleneterephthalate, e.g., polybutyleneterephthalate.

The following experimental examples are illustrative and non-limitative of the present invention.

EXAMPLE 1

172 g (1 mol) of hydroxymethylphenylphosphinic acid is heated at 150° C. inside a glass reactor of 500 ml of capacity, operating under a pressure of 50 mm$_{Hg}$, and water which evolves in vapour form is collected inside a cooled trap. After 5 hours, 9 g (0.5 mol) of water is collected, and the condensation rate decreases considerably.

The reaction mass is cooled, and 160.5 g of a solid product is recovered.

The $^{31}$P-N.M.R. analysis of the product dissolved in DMSO (dimethylsulphoxide) evidences the presence of the following molecular species:

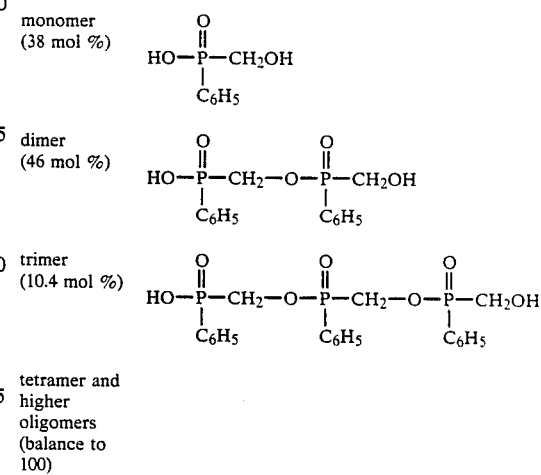

tetramer and higher oligomers (balance to 100)

Such a product can be represented in its whole by the general formula

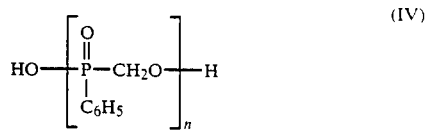

(IV)

wherein: n has the average value of 2.

EXAMPLE 2

172 g (1 mol) of hydroxymethylphenylphosphinic acid is heated at 180° C. inside a glass reactor of 500 ml of capacity, operating under a pressure of 0.1 mm$_{Hg}$. After 4 hours, 14.5 g (0.80 mol) of water is collected.

The reaction mass is cooled, and a solid product is recovered, which, at $^{31}$P-N.M.R. analysis shows the presence of a low percentage of monomer (<5%) and can be represented by the formula (IV) in Example 1, with an average value of n of about 5.

The equivalent weight of this product, as determined by titration with sodium, is of about 720.

EXAMPLE 3

100 g (0.50 mol) of isobutyl ester of hydroxymethylphenylphosphinic acid is heated at 180° C., under a high vacuum, together with 0.5 g of dibutyltin dilaurate. After 3 hours, during which isobutyl alcohol is removed, 70 g is recovered of a solid soluble in dimethylsulphoxide.

The $^{31}$P-N.M.R. analysis of the product evidences the oligomer nature of this product, which can be represented by the formula:

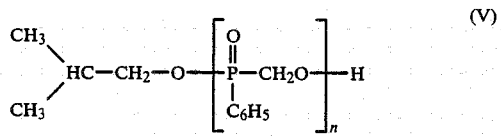

(V)

with an average value of n equal to about 35.

EXAMPLE 4

172 g (1 mol) of hydroxymethylphenylphosphinic acid is heated at 150° C. together with 158 g (1 mol) of phenylphosphonic acid on 250 ml of xylene. After 3 hours of reaction, during which approximately 8.5 g of water is removed, xylene is separated and about 300 g of a high-viscosity product is recovered.

The $^{31}$P-N.M.R. analysis of the product dissolved in dimethylsulphoxide (DMSO) evidences the presence of the following molecular species:

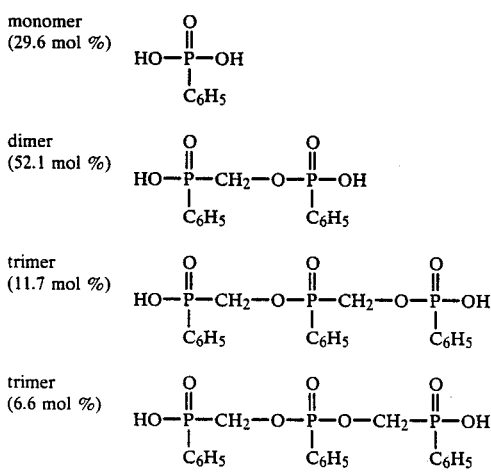

higher molecular weight products: negligible

The average degree of co-oligomerization is therefore equal to about 2.

EXAMPLE 5

To an autoclave, 1 part by weight (pbw) of ethylene glycol and 1.8 pbw pf terephthalic acid are charged.

The mixture is heated to the temperature of 235° C., under a pressure of 2 kg/cm$^2$, and the reaction is carried out in the presence of 0.03% by weight (relatively to terephthalic acid (of a quaternary aminic base, until a precondensate is obtained, which has an average molecular weight of approximately 500. This precondensate is used in the following experimental examples.

EXAMPLE 6

To an autoclave, 150 pbw of the precondensate of Example 5, 4.7 pbw of the product of oligomerization of hydroxymethylphenylphosphinic acid (obtained according to Example 1) is charged, together with 0.04% by weight (relatively to precondensate) of H$_3$PO$_4$ and Sb$_2$O$_3$. The mass is heated at 270°–280° C., and during a time of 1.5 hours the pressure is decreased from 760 torr to less than 1.0 torr.

The reaction is made proceed under vacuum for a further 2 hours, and at the end of this time period, a linear polyester is obtained, which has the following characteristics:

| | |
|---|---|
| intrinsic viscosity (as measured in o-chlorophenol at 25° C.) | 0.65 dl/g |
| COOH (free acidic groups) | 17 meq/kg |
| Tm (melting temperature, measured by means of differential thermal analysis) | 248° C. |
| DEG (% by weight of diethylene glycol) | 1.2% w/w |
| LOI ("Limiting oxygen index", ASTM 2863) (Oxygen index, measured on specimens obtained from polymer granules) | 30% vol. |
| Phosphorus (% by weight of phosphorus determined in the polymer) | 0.65% w/w |

EXAMPLE 7

150 pbw of the precondensate of Example 5, to which 0.04% by weight of H$_3$PO$_4$ and GeO$_2$ is added, is charged to an autoclave. The mass is heated to 270°–280° C. with stirring, and the pressure is reduced from 760 torr to less than 1.0 torr within a time of 1.5 hours. The reaction is allowed to proceed under vacuum for a further time of approximately 80 minutes and 4.5 pbw is then added of the product of oligomerization of hydroxymethylphenylphosphinic acid (obtained according to Example 3). The reaction is made proceed for a further 60 minutes, under the conditions of temperature and pressure as indicated above, and a linear polyester is obtained, which has the following characteristics:

| | |
|---|---|
| intrinsic viscosity | 0.65 dl/g |
| COOH | 25 meq/kg |
| Tm | 245° C. |
| DEG | 0.9% w/w |
| LOI | 30% vol. |
| Phosphoros | 0.63% w/w |

EXAMPLE 8

150 pbw of the precondensate of Example 6, containing 0.04% by weight of $H_3PO_4$ and $Sb_2O_3$ is charged to an autoclave. The mass is heated at 270°–280° C. and the pressure is reduced from 760 torr is less than 1 torr during a time of 1.5 hours.

The reaction is made proceed for a further 2 hours, and a linear polyester is obtained, which has the following characteristics:

| intrinsic viscosity | 0.642 dl/g |
|---|---|
| COOH | 14.8 meq/kg |
| Tm | 254° C. |
| DEG | 0.8% w/w |

The granules of the so-prepared polyester are blended with 3.5% by weight of the product of oligomerization of hydroxymethylphenylphosphinic acid (obtained according to Example 3). The blend is melted under an inert atmosphere for 35 minutes at 280° C. and is then kept under a pressure lower than 1 torr for the subsequent 30 minutes.

Thus, a linear polyester is obtained, which has the following characteristics:

| intrinsic viscosity | 0.62 dl/g |
|---|---|
| COOH | 27 meq/kg |
| Tm | 246° C. |
| DEG | 0.9% w/w |
| LOI | 30% vol. |
| Phosphorus | 0.5% w/w |

EXAMPLE 9

A master of linear polyester is prepared, which contains 30% by weight of the oligomerization product obtained in Example 3. This master is obtained by means of a copolymerization procedure similar to that of above Examples 6 and 7.

A further master is obtained, with a composition similar to the proceding one, by blending the product of oligomerization obtained in Example 3 with the preformed linear polyester and heating the blend under a high vacuum for 2 hours at 280° C., analogously to the preceding Example 8.

The so-obtained masters are added to the linear polyester during the spinning step, in such an amount as to give the fibre a phosphorus content (expressed as the element) of 0.6% by weight.

In this way, fibres of linear polyester are obtained, which have a LOI value higher than 30.

We claim:

1. A method of providing a linear polyester with flame-retarding properties comprising added a flame-retarding effective amount of a flame-retarding additive comprising a compound of the formula

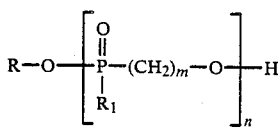

wherein:

R is selected from a hydrogen atom and a linear or branched chain alkyl group having from 1 to 6 carbon atoms;

$R_1$ is selected from unsubstituted phenyl; phenyl substituted with at least one substituent selected from an alkyl group having from 1 to 4 carbon atoms, an alkoxy group having 1 to 4 carbon atoms and a halogen atom; unsubstituted naphthyl; naphthyl substituted with at least one unsubstituent selected from an alkyl group having from 1 to 4 carbon atoms, an alkoxy group having from 1 to 4 carbon atoms, and a halogen atom; and an alkyl group having from 1 to 4 atoms;

m is an integer of 1, 2 or 3; and n is an integer of from 2 to 50.

2. The method of claim 1 wherein $R_1$ is unsubstituted phenyl.

3. The method of claim 1 wherein the amount of elemental phosphorous provided by the linear polyester is from 0.5 to 0.8% by weight based on the weight of the linear polyester containing the flame-retarding additive.

4. The flame-retarding linear polyester produced by the method of claim 1.

5. A method of providing a linear polyester with flame-retarding properties comprising adding a flame-retarding effective amount of flame-retarding additive during a polycondensation step of a precursor for forming the linear polyester whereby said flame-retarding additive coreacts with the precursor of the linear polyester such that the flame-retarding additive is chemically bonded to and evenly distributed throughout the linear polyester, said flame-retarding additive having the formula:

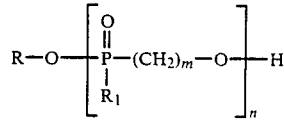

wherein:

R is selected from a hydrogen atom and a linear or branched chain alkyl group having from 1 to 6 carbon atoms;

$R_1$ is selected from unsubstituted phenyl; phenyl substituted with at least one substituent selected from an alkyl group having from 1 to 4 carbon atoms, an alkoxy group having 1 to 4 carbon atoms and a halogen atom; unsubstituted naphthyl; naphthyl substituted with at least one substituent selected from an alkyl group having from 1 to 4 carbon atoms, an alkoxy group having from 1 to 4 carbon atoms and a halogen atom; and an alkyl group having from 1 to 4 carbon atoms;

m is an integer of 1, 2 or 3; and n is an integer of from 2 to 50.

6. The method of claim 5 wherein $R_1$ is unsubstituted phenyl.

7. The method of claim 5 wherein the amount of elemental phosphorous provided by the flame-retarding additive is from 0.5 to 0.8% by weight based on the weight of the linear polyester containing the flame-retarding additive.

8. The flame-retarding linear polyester produced by the method of claim 5.

9. A method of providing a linear polyester with flame-retarding properties comprising:

reacting a linear polyester and 20 to 30% by weight of a flame-retarding additive to thereby form a master, reacting said master with a molten linear polyester to thereby obtain said flame-retarding linear polyester, the amount of the master being sufficient to provide 0.5 to 0.8% by weight of elemental phosphorous in said flame-retarding linear polyester, said flame-retarding additive having the formula:

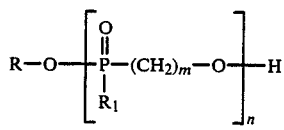

wherein:

R is selected from a hydrogen atom and a linear or branched chain alkyl group having from 1 to 6 carbon atoms;

$R_1$ is selected from unsubstituted phenyl; phenyl substituted with at least one substituent selected from an alkyl group having from 1 to 4 carbon atoms, an alkoxy group having 1 to 4 carbon atoms, and a halogen atom; unsubstituted naphthyl; naphthyl substituted with at least one substituent selected from an alkyl group having from 1 to 4 carbon atoms, an alkoxy group having 1 to 4 carbon atoms and a halogen atom; and an alkyl group having from 1 to 4 carbon atoms;

m is an integer of 1, 2 or 3; and n is an integer of from 2 to 50.

10. The method of claim 9 wherein $R_1$ is unsubstituted phenyl.

11. The flame-retarding linear polyester produced by the method of claim 9.

12. A flame-retarding additive having the formula

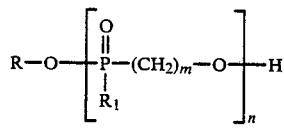

wherein:

R is selected from a linear or branched chain alkyl group having from 1 to 6 carbon atoms;

$R_1$ is selected from unsubstituted phenyl; phenyl substituted with at least one substituent selected from an alkyl group having from 1 to 4 carbon atoms, an alkoxy group having from 1 to 4 carbon atoms and a halogen atom; unsubstituted naphthyl, naphthyl substituted with at least one substituent selected from an alkyl group having from 1 to 4 carbon atoms, an alkoxy group having 1 to 4 carbon atoms and a halogen atom; and an alkyl group having from 1 to 4 carbon atoms;

m is an integer of 1, 2 or 3; and n is an integer of from 2 to 50.

13. The flame-retarding additive or claim 12 wherein $R_1$ is unsubstituted phenyl.

14. A flame-retarding additive having the formula

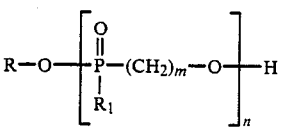

wherein:

R is a hydrogen atom;

$R_1$ is selected from unsubstituted phenyl; phenyl substituted with at least one substituent selected from an alkyl group having from 1 to 4 carbon atoms, an alkoxy group having from 1 to 4 carbon atoms and a halogen atom; unsubstituted naphthyl; naphthyl substituted with at least one substitulent selected from an alkyl group having from 1 to 4 carbon atoms, an alkoxy group having from 1 to 4 carbon atoms, and a halogen atom; and an alkyl group having from 1 to 4 carbon atoms;

m is an integer of 1, 2 or 3; and n is an integer of from 11 to 50.

15. The flame-retarding additive of claim 14 wherein $R_1$ is unsubstituted phenyl.

16. The flame-retarding additive of claim 15 wherein n is in the range of from 20 to 50.

17. The flame-retarding additive of claim 16 wherein m is 1.

18. A process for the preparation of a flame-retarding additive having the formula:

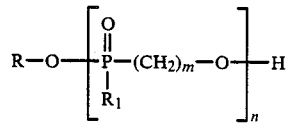

wherein:

R is a hydrogen atom;

$R_1$ is unsubstituted phenyl; phenyl substituted with at least one substituent selected from an alkyl group having from 1 to 4 carbon atoms, an alkoxy group having from 1 to 4 carbon atoms and a halogen atom; unsubstituted naphthyl; naphthyl substituted with at least one substituent selected from an alkyl group having from 1 to 4 carbon atoms, an alkoxy group having from 1 to 4 carbon atoms, and a halogen atom; and an alkyl group having from 1 to 4 carbon atoms;

m is an integer of 1, 2 or 3; and n is an integer of from 11 to 50, said process comprising: heating a compound of the formula

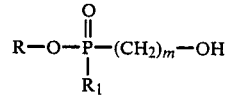

wherein:

R, $R_1$ and m are as defined above to a temperature of from 140° to 180° C. at a pressure of from 0.1 to 200 mmHg while removing any water or aliphatic alcohol formed during the reaction.

19. The process of claim 18 further comprising conducting the reaction in the presence of a solvent capable of forming an azeotropic mixture with water.

20. The process of claim 18 wherein $R_1$ is unsubstituted phenyl.

21. The process of claim 18 further comprising conducting the reaction in the presence of a catalyst selected from compounds containing tin, germanium, titanium, manganese, magnesium or zinc.

22. A process for the preparation of a flame-retarding additive of the formula

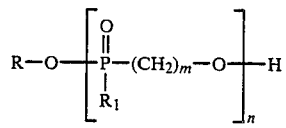

wherein:
R is selected from a hydrogen atom and a linear or branched chain alkyl group having from 1 to 6 carbon atoms;
$R_1$ is selected from unsubstituted phenyl; phenyl substituted with at least one substituent selected from an alkyl group having from 1 to 4 carbon atoms, an alkoxy group having from 1 to 4 carbon atoms and a halogen atom; unsubstituted naphthyl; naphthyl substituted with at least one substituent selected from an alkyl group having from 1 to 4 carbon atoms, an alkoxy group having from 1 to 4 carbon atoms, and a halogen atom; and
an alkyl group having from 1 to 4 carbon atoms;
m is an integer of 1, 2 or 3; and
n is an integer of from 2 to 50,
said process comprising:
reacting a compound having the formula

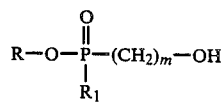

wherein:
R, $R_1$ and m are as defined above, with a compound having the formula

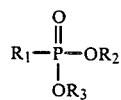

wherein:
$R_1$ is as defined above
$R_2$ and $R_3$ are the same or different from each other and are selected from a hydrogn atom and a linear or branched chain alkyl group having from 1 to 6 carbon atoms, to a temperature of from 140° to 180° C. at a pressure of 0.1 to 200 mmHg while removing any water or aliphatic alcohol formed during the reaction.

23. The process of claim 22 further comprising conducting the reaction in the presence of a solvent capable of forming an azeotropic mixture with water.

24. The process of claim 22, wherein $R_1$ is unsubstituted phenyl.

25. A process for the preparation of a flame-retarding additive having the formula

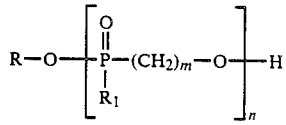

wherein:
R is selected from a linear or branched chain alkyl group having 1 to 6 carbon atoms;
$R_1$ is selected from unsubstituted phenyl; phenyl substituted with at least one substituent selected from an alkyl group having from 1 to 4 carbon atoms, an alkoxy group having from 1 to 4 carbon atoms and a halogen atom; unsubstituted naphthyl; naphthyl substituted with at least one substituent selected from an alkyl group having from 1 to 4 carbon atoms, an alkoxy group having from 1 to 4 carbon atoms, and a halogen atom; and an alkyl group haing from 1 to 4 carbon atoms;
m is an integer of 1, 2 or 3; and
n is an integer of from 2 to 50, said process comprising:
heating a compound of the formula

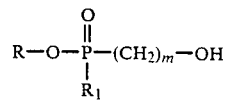

wherein:
R, $R_1$ and m are as defined above to a temperature of from 140° to 180° C. at a pressure of from 0.1 to 200 mmHg while removing any water or aliphatic alcohol formed during the reaction.

26. The process of claim 25 wherein $R_1$ is unsubstituted phenyl.

27. The process of claim 25 further comprising conducting the reaction in the presence of a catalyst selected from compounds containing tin, germanium, titanium, manganese, magnesium or zinc.

28. The process of claim 27 wherein the catalyst is an alkali metal alkoxide.

* * * * *